(12) United States Patent
Seeger et al.

(10) Patent No.: US 10,610,738 B2
(45) Date of Patent: Apr. 7, 2020

(54) SENSORIMOTOR DEVICE FOR EXERCISE AND REHABILITATION

(71) Applicant: iBalanS LLC, Somers Point, NJ (US)

(72) Inventors: Diena L. Seeger, Berlin, NJ (US); Kerri A. Nelson, Marlton, NJ (US)

(73) Assignee: iBalanS LLC, Somers Point, NJ (US)

( * ) Notice: Subject to any disclaimer, the term of this patent is extended or adjusted under 35 U.S.C. 154(b) by 0 days.

(21) Appl. No.: 15/320,051

(22) PCT Filed: Jun. 18, 2015

(86) PCT No.: PCT/US2015/036339
§ 371 (c)(1),
(2) Date: Dec. 19, 2016

(87) PCT Pub. No.: WO2015/195859
PCT Pub. Date: Dec. 23, 2015

(65) Prior Publication Data
US 2017/0197114 A1 Jul. 13, 2017

Related U.S. Application Data

(60) Provisional application No. 62/013,859, filed on Jun. 18, 2014.

(51) Int. Cl.
*A63B 26/00* (2006.01)
*A63B 71/06* (2006.01)
(Continued)

(52) U.S. Cl.
CPC .......... *A63B 26/003* (2013.01); *A61B 5/6895* (2013.01); *A63B 4/00* (2013.01);
(Continued)

(58) Field of Classification Search
CPC .............. A63B 21/008; A63B 21/0602; A63B 21/0004; A63B 21/072–085; A63B 21/06003; A63B 26/003
See application file for complete search history.

(56) References Cited

U.S. PATENT DOCUMENTS 4,986,535 A 1/1991 Hull et al.
5,056,778 A * 10/1991 Hull .................... A63B 21/0602
482/105

(Continued)

FOREIGN PATENT DOCUMENTS

SU 1437044 A1 11/1988

OTHER PUBLICATIONS

Int'l Preliminary Report on Patentability dated Dec. 20, 2016 in PCT/US2015/036339.

(Continued)

*Primary Examiner* — Jennifer Robertson
(74) *Attorney, Agent, or Firm* — Panitch Schwarze Belisario & Nadel LLP

(57) ABSTRACT

A sensorimotor exercise device including a casing is provided. The casing includes an elongated center member having a first end and a second end, a first end member provided at the first end of the center member and a second end member provided at the second end of the center member. The casing also includes a low viscosity fluid at least partially filing a hollow interior of the sensorimotor exercise device. The center member has a cylindrical shape and the first and second end members have a tapered configuration. A diameter of each of the first and second end members increasing from a first end thereof toward an opposing second end thereof.

22 Claims, 7 Drawing Sheets

(51) Int. Cl.

| | |
|---|---|
| *A63B 21/06* | (2006.01) |
| *A63B 21/072* | (2006.01) |
| *A63B 23/035* | (2006.01) |
| *A63B 21/00* | (2006.01) |
| *A63B 4/00* | (2006.01) |
| *A63B 21/068* | (2006.01) |
| *A61B 5/00* | (2006.01) |
| *A63B 23/12* | (2006.01) |
| *A63B 23/04* | (2006.01) |
| *A63B 21/075* | (2006.01) |
| *A63B 22/20* | (2006.01) |
| *A63B 23/02* | (2006.01) |
| *A63B 22/00* | (2006.01) |

(52) U.S. Cl.
CPC ...... *A63B 21/0004* (2013.01); *A63B 21/0602* (2013.01); *A63B 21/068* (2013.01); *A63B 21/0724* (2013.01); *A63B 23/03525* (2013.01); *A63B 23/0405* (2013.01); *A63B 23/1209* (2013.01); *A63B 71/0622* (2013.01); *A61B 2503/08* (2013.01); *A61B 2503/10* (2013.01); *A63B 21/0603* (2013.01); *A63B 21/075* (2013.01); *A63B 21/4035* (2015.10); *A63B 22/20* (2013.01); *A63B 23/0211* (2013.01); *A63B 2022/0092* (2013.01); *A63B 2023/0411* (2013.01); *A63B 2071/0625* (2013.01); *A63B 2071/0652* (2013.01); *A63B 2071/0655* (2013.01); *A63B 2071/0694* (2013.01); *A63B 2208/0204* (2013.01); *A63B 2208/0219* (2013.01); *A63B 2208/0228* (2013.01); *A63B 2220/10* (2013.01); *A63B 2220/51* (2013.01); *A63B 2220/52* (2013.01); *A63B 2225/50* (2013.01)

(56) References Cited

U.S. PATENT DOCUMENTS

| | | | |
|---|---|---|---|
| 6,217,495 B1* | 4/2001 | Yalch | A63B 15/00 473/256 |
| 6,224,517 B1* | 5/2001 | Dereszynski | A63B 21/0602 482/105 |
| 6,312,364 B1* | 11/2001 | Selsam | A63B 21/06 206/501 |
| 2005/0065002 A1* | 3/2005 | Su | A63B 21/075 482/106 |
| 2010/0069206 A1* | 3/2010 | Viselman | A63B 21/072 482/106 |
| 2012/0245000 A1 | 9/2012 | Burke | |
| 2013/0196830 A1* | 8/2013 | Pfitzer | A63B 21/0602 482/110 |

OTHER PUBLICATIONS

Int'l Search Report dated Sep. 3, 2015 in PCT/US2015/036339.
www.wavebar.net, see website printout, dated at least as early as Jun. 17, 2014.

* cited by examiner

SENSORIMOTOR DEVICE FOR EXERCISE AND REHABILITATION

CROSS-REFERENCE TO RELATED APPLICATIONS

This application claims priority to U.S. Provisional Patent Application No. 62/013,859, filed on Jun. 18, 2014, entitled "Sensorimotor Device for Exercise and Rehabilitation," the entire contents of which are incorporated by reference herein.

BACKGROUND OF THE INVENTION

An embodiment of the present invention relates generally to a fitness and rehabilitation device designed for use by children, adults, seniors, athletes and sedentary people. More particularly, the fitness and rehabilitation device of the present invention is suitable for use by any individual who may benefit from improved proprioceptive and sensorimotor skills, balance and overall fitness. The fitness and rehabilitation device of the present invention is also suitable for use by any individual who wants or needs to facilitate motor learning, improve reaction time, and/or improve equilibrium strategies. The fitness and rehabilitation device of the present invention also provides a key health benefit, as it is well known that faster muscle reaction is better protection than strength alone for the prevention of injury. The fitness and rehabilitation device of the present invention may be used as a stand-alone device or may be integrated into a routine with other devices.

The sensory system plays a key role in proper motor function. Body movement (i.e., motor function) efficiency can be honed through training a subconscious, complex sequence of muscle activation and timing specific to the task at hand. As such, a comprehensive exercise training or rehabilitation program should include reflexively training for unpredictability.

Sensorimotor training tools provide stimulation and integration of improved movement and motor strategies. Compared with strength training alone, sensorimotor training has been proven to better improve proprioception (e.g., sense of position, posture and movement), muscle reaction, postural stability and strength. Further, the ability to maintain balance is fundamental to achieving more advanced perceptual motor activities. Balance mechanisms, along with visual and tactile information and proprioceptive feedback, provide the knowledge for perceiving body orientation in space.

However, balance, defined as the ability to maintain equilibrium while engaging in various locomotor or non-locomotor activities, may be partially or totally deficient for some people. In particular, the elderly often lack the postural adjustments and equilibrium reactions which comprise the basic movement patterns necessary for balance and proper posture. Where these reactions are deficient, they must be taught or developed through appropriate exercise and/or physical therapy. Training automatic reactions to unexpected loads best assists in developing these reactions or basic controls.

Prior art devices for such exercise and/or physical therapy activities are known. However, generally stated, the known prior art devices merely provide a means for improving an individual's balancing skills on a particular device and do not simulate the balance conditions actually encountered in everyday life, which is stability underfoot and instability in the rest of the body. Other prior art devices rely on the users themselves to use force to generate instability, rather than having the instability inherent in the device itself.

Some prior art exercise devices utilize fluid, typically water, contained in the device. For example, some prior art devices utilize water as a replacement for a weight, such as a dumbbell filled with water instead of metal or sand (see, for example, U.S. Design Pat. No. D633,155). Another example is "slosh pipes," depicted in videos currently found on the internet, which are typically homemade water-filled PVC pipes capped at both ends to permanently seal the water inside. Typically, however, such homemade prior art devices are of a size, weight and length (e.g., 4 inches in diameter, 20 pounds with sand and water, and 5-6 feet long) that make it extremely difficult to manage the device and even to grip the device by hand. Indeed, even just the casing (i.e., the PVC pipe) of such prior art devices, before the device is filled with fluid, can weigh 3 or more pounds.

Other known prior art devices allow for the fluid (e.g., water) to be emptied therefrom by the user to reduce the weight of the device during transport and facilitate lighter weight travel. Such devices can then be filled again when the user arrives at his/her desired location to add the weight back to the device (see, for example, U.S. Design Pat. No. D633,155). Other devices use water as a simple way to allow the user to create a desired variable weight device by letting the user fill the device with water to certain markers. Thus, in the known prior art devices, the fluid is merely a means of adding weight to the bar or device and is not included as a necessary functional aspect of the device.

Accordingly, it would be desirable to provide an exercise and/or rehabilitation device which simulates the balance conditions actually encountered in everyday life, which is relatively lightweight and easy to manage and handle, and which includes a fluid element as a necessary functional aspect of the device so as to improve the skill and reflex of the user.

BRIEF SUMMARY OF THE INVENTION

One objective of a preferred embodiment of the present invention is to provide a sensorimotor exercise device that is used as part of a functional stability training program aimed at improving motor strategies and resulting in better balance, strength, coordination, mobility, speed and power in athletic and everyday activities, as well as reducing the chance of future injury and overuse issues.

Preferably, the sensorimotor exercise device can be used or applied in an infinite variety of exercises for rehabilitation, such as lifting, balancing, bending, twisting, flexion, extension or the like. Preferably, the sensorimotor exercise device is particularly applicable to movements that are more natural and functional representations of activities of daily living, with the goal of enhancing dynamic stability and functional joint stability of the user.

Another objective of a preferred embodiment of the present invention is to provide a sensorimotor exercise device capable of being used in general fitness, Pilates exercises, and rehabilitation applications. Preferably, the sensorimotor exercise device is a self-limiting exercise device which demands mindfulness and an awareness of movement, alignment, balance and control.

Another objective of a preferred embodiment of the present invention is to provide a sensorimotor exercise device capable of stimulating the nervous system with sensory information at all three reflexive levels, in order to improve motor control integration.

Another objective of a preferred embodiment of the present invention is to provide a sensorimotor exercise device which gives the home user and/or professional user valuable awareness of the user's true position, posture, strength, balance and ability.

Yet another objective of a preferred embodiment of the present invention is to provide sensorimotor exercise equipment which requires no preparation method for engagement (e.g., no refilling or emptying water), is aesthetically pleasing, and is easy to handle.

In particular, in one embodiment, the present invention is directed to a sensorimotor exercise device that includes a casing having an elongated center member with a first end and a second end, a first end member provided at the first end of the center member and a second end member provided at the second end of the center member. The sensorimotor exercise device further includes a low viscosity fluid at least partially filing a hollow interior of the sensorimotor exercise device. The center member has a cylindrical shape and the first and second end members have a tapered configuration. A diameter of each of the first and second end members increases from a first end thereof toward an opposing second end thereof.

BRIEF DESCRIPTION OF THE SEVERAL VIEWS OF THE DRAWINGS

The following detailed description of a preferred embodiment of the present invention will be better understood when read in conjunction with the appended drawings. For the purposes of illustrating the invention, there is shown in the drawings an embodiment which is presently preferred. It is understood, however, that the invention is not limited to the precise arrangements and instrumentalities shown. In the drawings.

DETAILED DESCRIPTION OF THE INVENTION

Figure 1:
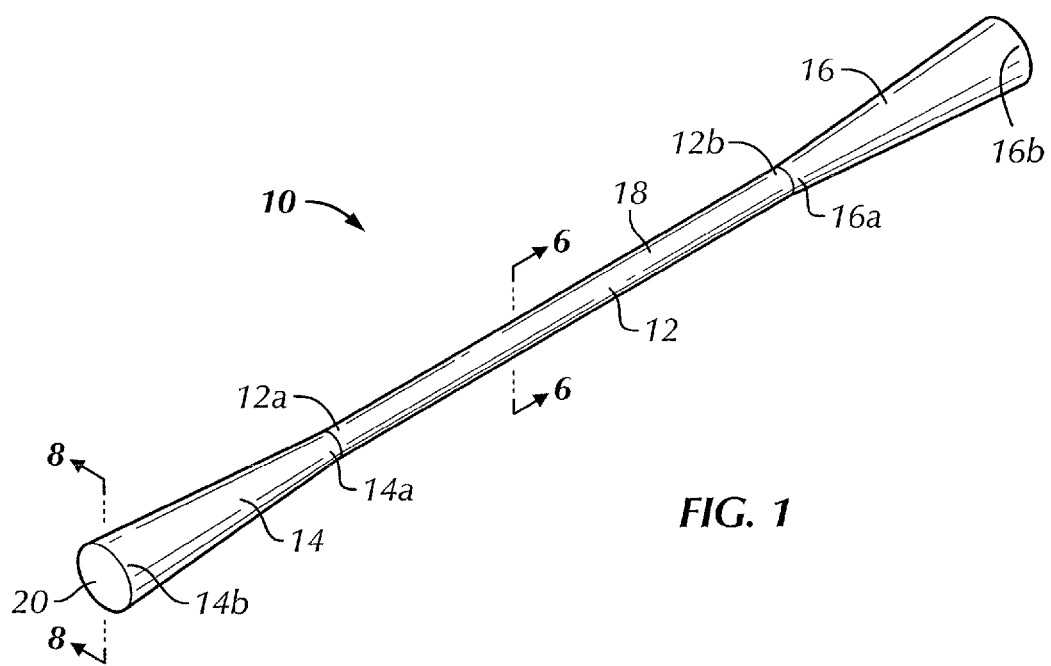
FIG. 1 is a front left perspective view of an exercise device in accordance with a preferred embodiment of the present invention.

Certain terminology is used in the following description for convenience only and is not limiting. The words "right", "left", "lower", and "upper" designate directions in the drawings to which reference is made. The words "inwardly" and "outwardly" refer to directions toward and away from, respectively, the geometric center of the device and designated parts thereof. The terminology includes the above-listed words, derivatives thereof, and words of similar import. Additionally, the words "a" and "an", as used in any claims and in the corresponding portions of the specification, mean "at least one."

Referring to the drawings in detail, wherein like numerals and characters indicate like elements throughout, there are shown in FIGS. 1-11 presently preferred embodiments of an exercise and rehabilitation device, and more particularly a sensorimotor exercise and rehabilitation device, in accordance with the present invention.

With particular reference to FIG. 1, the exercise and rehabilitation device, generally designated 10 and referred to hereinafter as an "exercise device" for the sake of brevity, comprises an elongated center tubular member 12, a first end member 14 provided at a first end 12a of the center tubular member 12, and a second end member 16 provided at a second end 12b of the center tubular member 12. The center member 12 is preferably a rigid tubular member which is at least partially hollow and thus has a bore extending therethrough. The first and second end members 14, 16 are preferably of equal length and are mirror images of each other. More particularly, the first and second end members 14, 16 are generally cylindrical in shape, at least partially hollow and have a fluted or tapered configuration. That is, the circumference of each end member 14, 16 is tapered, such that the circumference gradually and steadily increases from a first end 14a, 16a of each end member 14, 16 to an opposing second end 14b, 16b thereof. Taken together, the center member 12 and the first and second end members 14, 16 form a casing 18 of the exercise device 10.

The exercise device 10 is of a sufficient length L (see FIGS. 3 and 4) so as to extend a substantial distance to either side of the median sagittal plane and longitudinal axis of the body of a user. Generally, the median sagittal plane and longitudinal axis span approximately four to seven feet for the average adult and approximately two to four feet for children. The length L of the exercise device 10 ensures that the device 10 is manageable when rested on a lateral lower extremity in the lateral decubitus position.

The exercise device 10 can be constructed from any material, such as but not limited to fiberglass, composite, plastic, resin, metal, such as aluminum, or any such suitable material that is known or invented in the future that provides suitable strength, durability, weight and leak proof properties to support exercise and rehabilitation activities using the exercise device 10. It will be understood that the center member 12 and the first and second end members 14, 16 need not be constructed of the same material, and may be constructed of different appropriate materials. The exercise device 10 may be constructed from any conventional production method, such as but not limited to rotational molding, blow molding, thermoforming, 3-D printing or any known method or suitable method that is invented in the future that results in the device 10 having the desired properties to support the desired exercise and rehabilitation activities.

Preferably, the exercise device 10 is strong enough to withstand body pressure and weight exerted on any portion of the exterior casing 18 thereof during use. For example, a typical user could exert 20 lbs of pressure on the center member 12 during some movements. In addition, the exercise device 10 is preferably fracture and impact resistant when dropped from a position of about nine feet from the ground (i.e., likely the maximum height if raised overhead by an adult). While the mechanical strength of the casing 18 is important, it is also important that the casing 18 itself is very lightweight. Preferably, the casing 18 accounts for approximately 20% of the total weight of the fully constructed exercise device 10. Also, for a typical adult dimension, the casing 18 preferably weighs approximately one pound or so, such that the casing 18 is lightweight and allows for a high degree of instability due to the fluid contained within the casing 18 (as described below). It will be understood that the weight of the casing 18 will vary based on the dimensions of the intended user in order to provide the desired degree of instability.

In one embodiment, the center member 12 and the first and second end members 14, 16 are made from one or more polymeric materials. It will be understood that the center member 12 and the first and second end members 14, 16 may be made from the same polymer or from different polymers. As a non-limiting example, the center member 12 may be extruded from Delrin® and the first and second end members 14, 16 may be blow molded with a linear low density polyethylene. Preferably, the materials of the center member 12 and the first and second end members 14, 16 have a relatively high durometer or hardness. It will be understood that the center member 12 and the first and second end members 14, 16 may be made from any suitable material having a relatively high durometer or hardness.

The finished look of the exterior surface of the casing 18 can be that of a solid color, patterns, translucent or some combination thereof, whatever is deemed esthetically pleasing and/or functionally stimulating to the intended user and does not distract from key functional elements (such as hand placement described below) of the exercise device 10.

Figure 2:
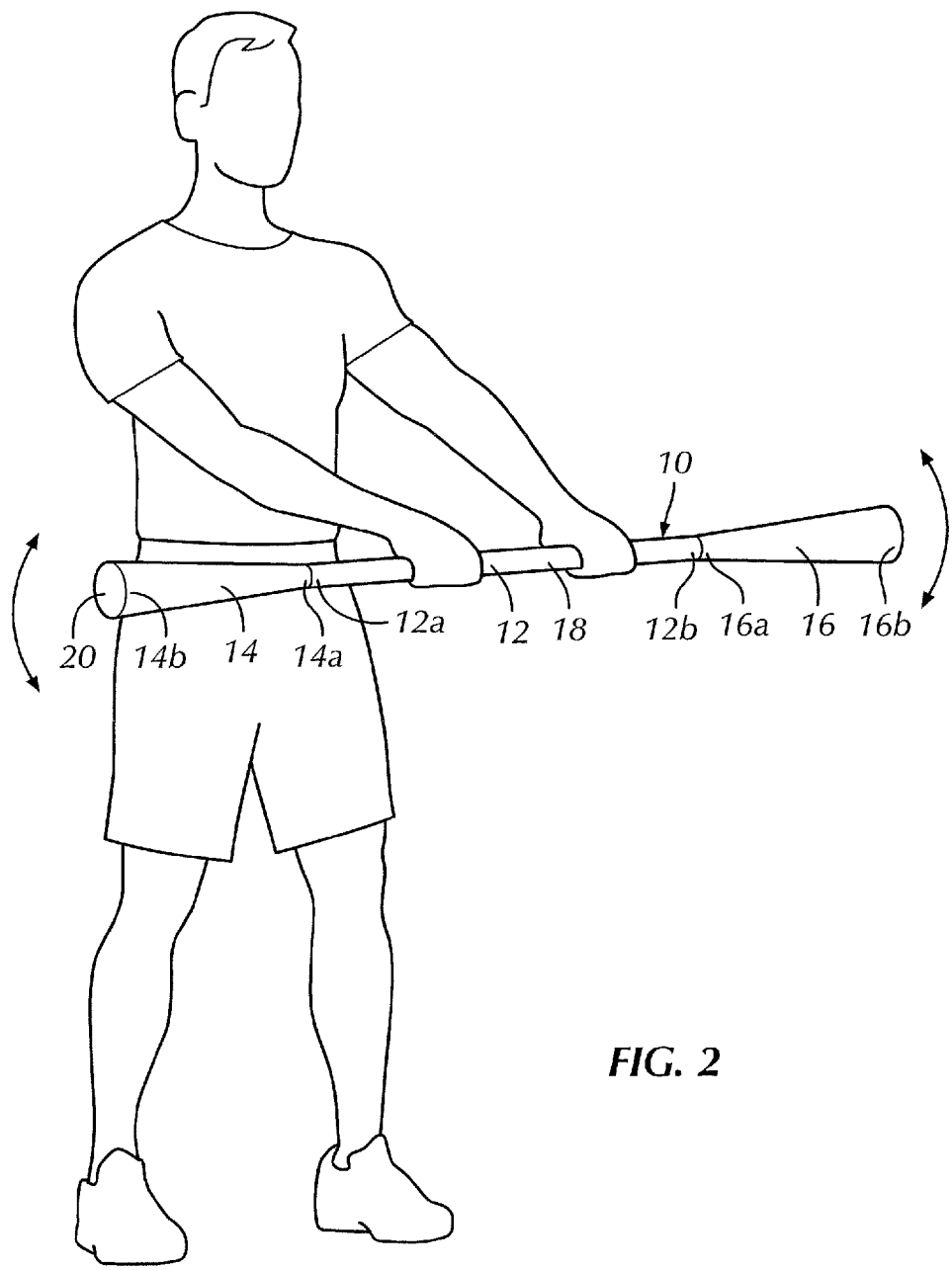
FIG. 2 is a perspective view of the exercise device shown in FIG. 1 while being handled by a user in a first position.

Referring to FIG. 2, the exercise device 10 is shown while being held in a standard hand grip position. Due to the size, shape and contours of the exercise device 10, the center member 12 is sufficiently long enough to allow for a greater than shoulder width two-hand grip position as shown in FIG. 2. The grip width will vary based on the intended user. For example, for an average female adult, the grip width is roughly between twenty two and twenty six inches. The diameter of the center member 12 is preferably as large as possible so as to allow a rapid and uninterrupted flow of a fluid 24 housed within the casing 18, while providing a comfortable feel when loosely gripped by a user's hand (see FIG. 6).

Figure 3:
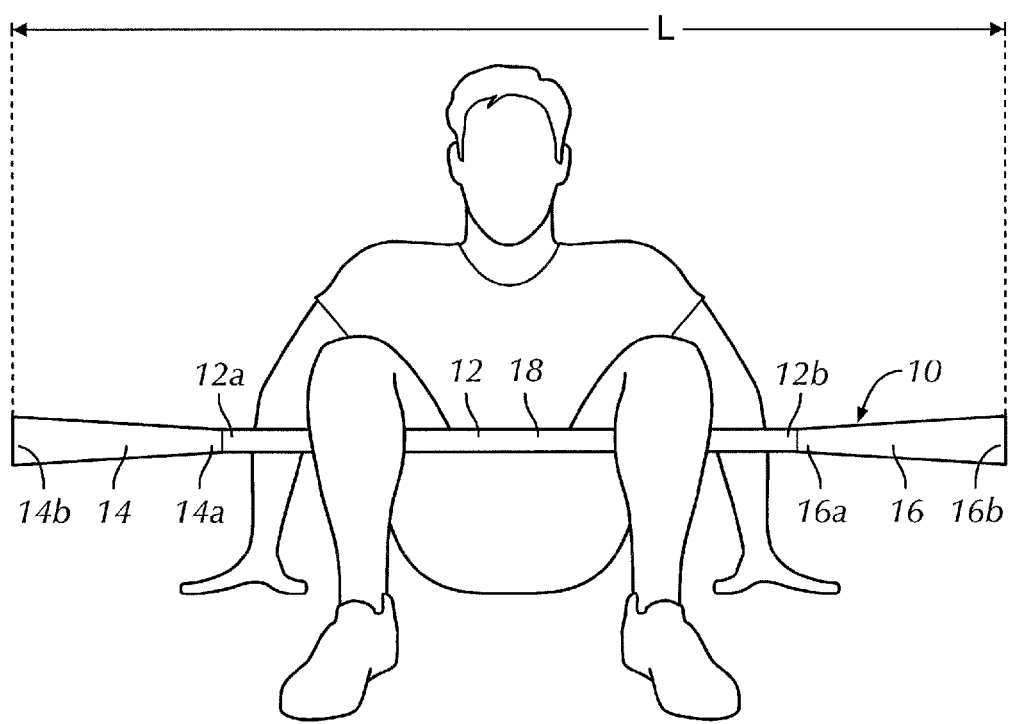
FIG. 3 is a front elevational view of the exercise device shown in FIG. 1 while being handled by a user in a second position.

In addition, the diameter of the center member 12 preferably enables the exercise device 10 to be held in the fold of a user's knees (as illustrated in FIG. 3) or elbows, rested on a user's shoulders, or managed in another potential body position. The diameter of the center member 12 will therefore vary based on the size of the intended user of the exercise device 10. In one embodiment, wherein the user is an average female adult, the diameter of the center member 12 is approximately 1.5 inches. The diameter of the second ends 14b, 16b of the end members 14, 16 of the exercise device 10 is preferably approximately two to three times larger than that of the center member 12 to generate the desired torque and hence instability of the exercise device 10 to support the desired exercise and rehabilitation activities.

Figure 4:
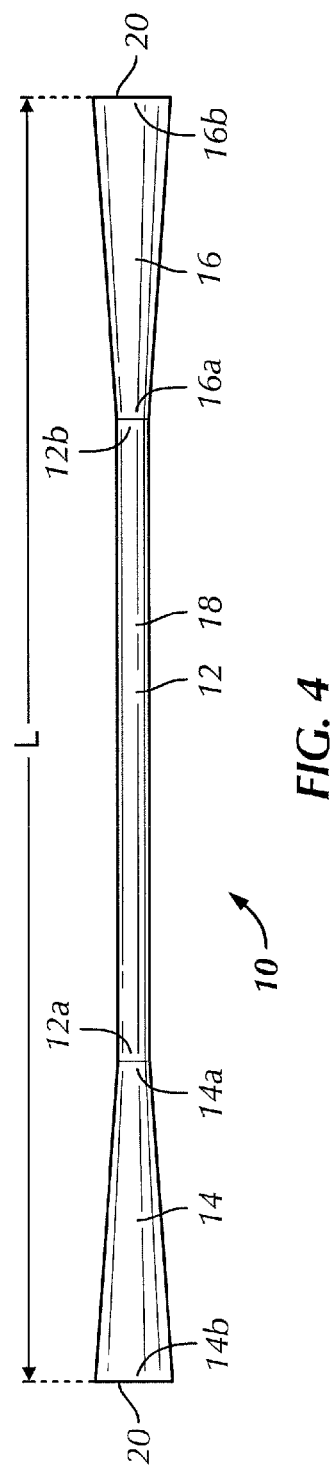
FIG. 4 is a front elevational view of the exercise device shown in FIG. 1.
Figure 5:
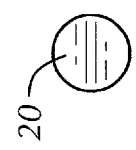
FIG. 5 is a right elevational view of the exercise device shown in FIG. 1.

Referring to FIGS. 4 and 5, in one embodiment, the circular fluted ends 14b, 16b of the first and second end members 14, 16 are provided with caps 20. The caps 20 may be integrally formed with the first and second end members 14, 16, such as when the first and second end members 14, 16 are formed by blow molding, or may be secured thereto by any suitable device or method that forms a tight seal with the second ends 14b, 16b and does not interrupt the flow of the fluid 24 (FIGS. 8-10) contained within the casing 18. Depending on the fabrication method utilized to form the casing 18, the entire casing 18 may be one piece or several pieces joined by a machine, adhesion or other suitable method, such that the casing 18 has a unitary and integral appearance and exhibits the desired strength, durability, weight and leak proof properties to support the desired exercise and rehabilitation activities. The perimeters of the end caps 20 are preferably constructed to be sufficiently durable, yet pliable enough to break and fall (as this is the most likely point of impact if the exercise device 10 were dropped) so that none of the other components are damaged.

Figure 6:
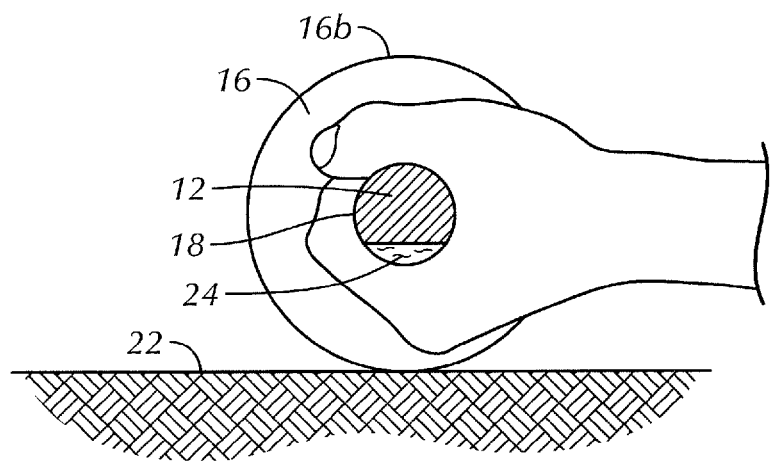
FIG. 6 is an enlarged cross-sectional view of the exercise device shown in FIG. 1, taken along line 6-6, while being gripped by a user in a first direction.
Figure 7:
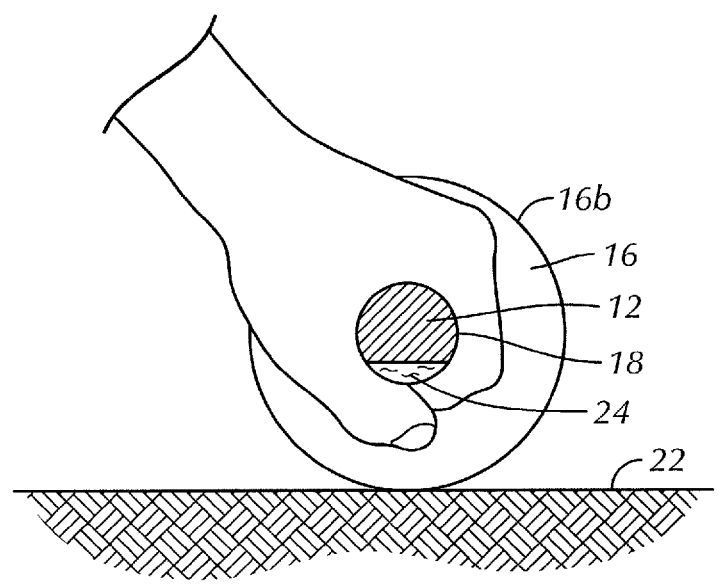
FIG. 7 is an enlarged cross-sectional view of the exercise device shown in FIG. 1, taken along line 6-6, while being gripped by a user in a second direction.

Also, the difference between the circumference or diameter of the center member 12 and the second ends 14b, 16b of the first and second end members 14, 16 is such that there is sufficient clearance for the user to put his/her hands under the center member 12 when the exercise device 10 is resting on a flat horizontal surface 22, as shown in FIGS. 6 and 7. Thus, the exercise device 10 can be easily "scooped up" or levitated from a resting position on the ground or floor surface 22 without requiring rolling or moving of the device 10. This is important to allow completion of various movements that require grasping of the exercise device 10 when it is rested in the horizontal position on a flat surface 22, such as the ground or an exercise floor.

Preferably, the casing 18 is leak-proof. In one embodiment, the fluid 24 encapsulated within the leak-proof casing 18 is preferably a high density, low viscosity fluid 24, and more preferably a non-evaporating, biologically safe fluid 24 (see FIGS. 6-10). In one embodiment, the fluid 24 preferably has a viscosity of 0.5 to 100 cP, and more preferably 0.5 to 7 cP, and preferably has a density of 0.8 to 3 g/mL, and more preferably 1.75 to 2.75 g/mL.

Preferably, the fluid 24 only partially fills the bore or interior of the casing 18, such that as the exercise device 10 is tilted, there is a resulting proper movement of the fluid 24 within the casing 18. The fluid 24 may be any suitable fluid, in the form of a liquid or a gas, as long as it is capable of sufficient flow within the casing 18 and accounts for the reaction times of the intended user. For example, the fluid 24 may be a gas with liquid-like flow properties.

Preferably, the fluid 24 cannot be added or removed from the casing 18 by a user. Thus, the fluid 24 is a fundamental and integral component of the device 10 itself. Preferably, the fluid 24 is of a proper viscosity and density based on the condition of the intended user and included at the prescribed level to create the device instability required to achieve the desired results of the device 10. More particularly, the fluid 24 housed within the casing 18 may vary depending upon the skill and reflex of the intended user of the exercise device 10. For example, in one embodiment, wherein the exercise device 10 is configured to be used by an athlete, the fluid 24 contained in the casing 18 preferably has a relatively low viscosity (e.g., approximately 0.8 cP). In another embodiment, in which the exercise device 10 is designed for use by an elderly rehabilitation patient, the viscosity of the fluid 24 contained in the casing 18 is preferably a bit higher (e.g., approximately 7 cP) than the viscosity of the fluid 24 contained in the exercise device 10 when designed for an athlete. Thus, the exercise device 10 is configured to contain fluids of varying viscosity so as to accommodate the skill and reflex of the intended user. The viscosity of the fluid 24 determines how fast a tilt in the device 10 will result in reaching maximum torque, as described below.

Figure 8:
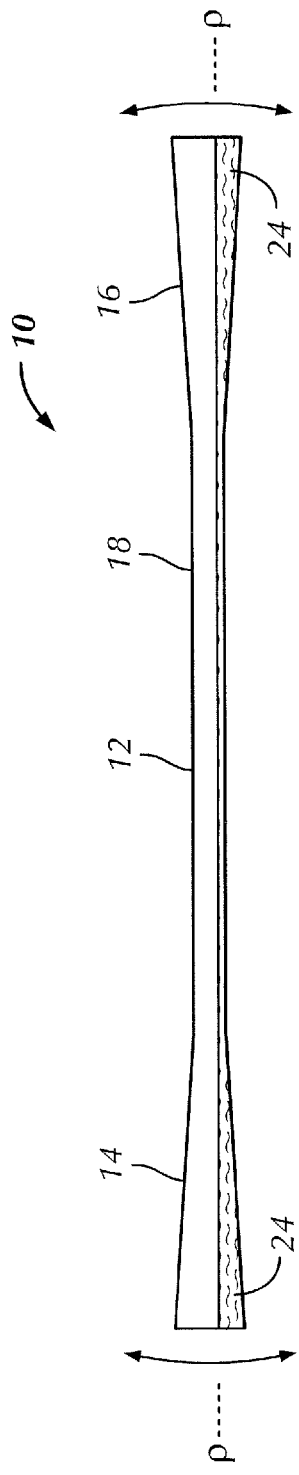
FIG. 8 is a front cross-sectional elevational view of the exercise device shown in FIG. 1, taken along line 8-8.
Figure 9:
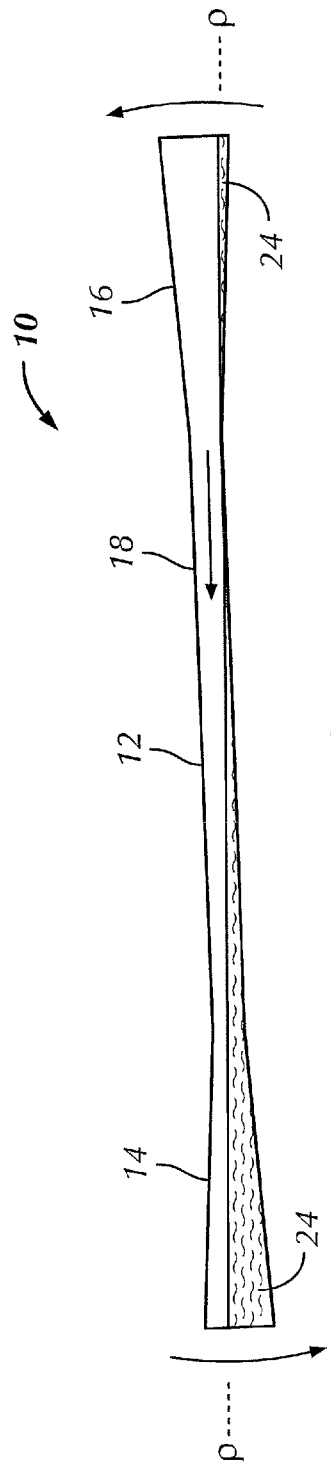
FIG. 9 is a front cross-sectional elevational view of the exercise device shown in FIG. 1, taken along line 8-8, while being tilted in a first direction.
Figure 10:
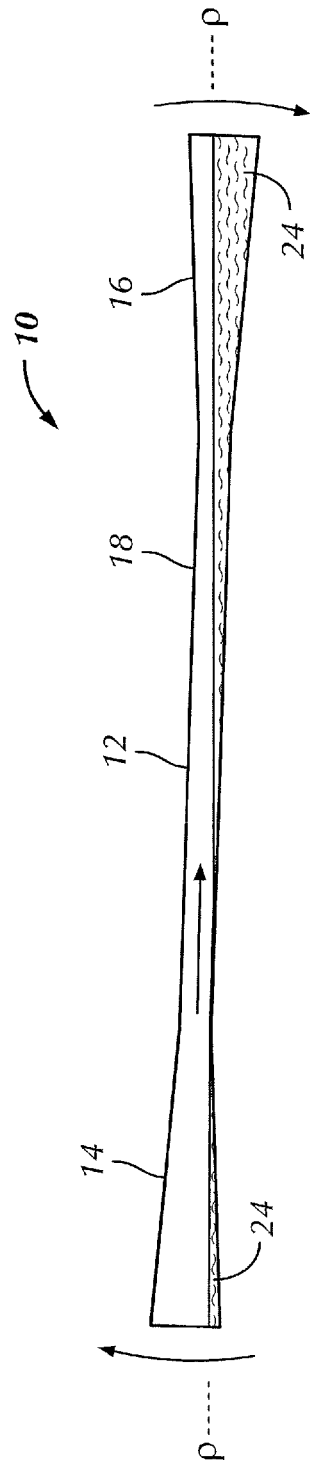
FIG. 10 is a front cross-sectional elevational view of the exercise device shown in FIG. 1, taken along line 8-8, while being tilted in a second direction.

Referring to FIG. 8, the exercise device 10 is shown in a completely horizontal position with respect to a longitudinal plane P that is parallel to a floor or ground surface. Referring to FIG. 9-10, when the exercise device 10 is slightly tilted in either a first direction (FIG. 9) or an opposite second direction (FIG. 10), such that the horizontal plane P is only slightly broken, the fluid 24 contained within the casing 18 preferably exhibits a reciprocating movement within the exercise device 10. Such a reciprocating movement, in turn, forces return of the fluid 24 toward a tail end (i.e., the end which is at least slightly vertically below the horizontal plane P) of the exercise device 10 and creates momentum caused by the fluid 24 moving against the internal portion of the leading end (i.e., the end which is at least slightly vertically above the horizontal plane P) of the exercise device 10. This creates an unstable surface which, in turn, automatically prompts the user of the exercise device 10 to work to re-correct and establish stability.

Because of the fluted shape of the second ends 14b, 16b of the end members 14, 16, a relatively high torque is generated by the exercise device 10 when it is tilted even just slightly (e.g., even less than one degree). The generated torque increases as the exercise device 10 is tilted to a greater degree. Compared with prior art devices which generally utilize a casing of constant diameter, the torque generated by the exercise device 10 may be double or more when tilted three to five degrees. For example, the torque of a constant diameter prior art device (i.e., no fluted shaped ends) is approximately 0.2 Nm when approaching a five degree tilt, while the torque generated by the exercise device 10 is approximately 0.4 Nm when approaching the same degree of tilt. This torque enables much greater instability, even with relatively small diameter tubing in the grip area of the center member 12.

The exercise device 10 is preferably configured such that when a user holds the exercise device 10 in a dual grip position, such as a two hand grip (FIG. 2), or behind the knees (FIG. 3), the user grips the exercise device 10 at locations that are equidistant from the midpoint of the center member 12 to enable a balanced load across the user's body. As such, in one embodiment, the exercise device 10 preferably includes tactile, visual and/or audible indicators (not shown) of the midpoint of the center member 12, as well as tactile, visual and/or audible indicators 26 of at least two (and more preferably various) points that are equidistant from either side of the midpoint (see FIG. 11).

Preferably, the user is able to recognize or identify the midpoint and equidistant points and the associated indicators 26 when the exercise device 10 is both in view (such as held out in front with arms extended) and out of view (such as held above head when lying in a horizontal position). As such, the indicators 26 are preferably designed to allow for a comfortable yet easily identifiable feedback that the user has his/her hands properly placed at points equidistant from the midpoint of the center member 12. The indicators 26 may be in any appropriate form, such as but not limited to color markings at the appropriate locations on the casing 18, projections or indentations at the appropriate locations of the casing 18, a change of texture at the appropriate locations of the casing 18, or the like. In addition, the indicators 26 preferably give the user feedback as to the difficulty level they are engaging with the exercise device 10, as a closer hand grip to the midpoint increases the difficulty level of the exercise. This can be a self-imposed difficulty level or one instructed by a rehabilitation specialist or fitness instructor when cueing the user for a movement including the exercise device 10.

Regardless of grip position and type of grip (e.g., one or two-hand knee, elbow, hip etc.), the exercise device 10 is configured, among other things, to be used with movements that include maintaining a stable horizontal plane P with the exercise device 10 or purposefully breaking the horizontal plane P and then returning to the stable horizontal plane P.

In one embodiment, when precision balancing is required (e.g., for a trained athlete), a user may want to be able to recognize when the exercise device 10 is levelly positioned with respect to the horizontal plane P. In such an embodiment, the exercise device 10 preferably includes tactile, visual and/or audible indicators (not shown) of whether the exercise device 10 is levelly positioned with respect to the horizontal plane P. Examples of such indicators include, but are not limited to, a liquid bubble indicator, laser and light indicators, or vibration of the exercise device 10. Any such indicators preferably allow for comfortable, yet easily identifiable feedback about the positioning of the exercise device 10 with respect to the horizontal plane P. This is a very important feedback cue and measure for areas of needed improvement regarding balance and asymmetrical movement. Further, such information forms important self-education for the user and feedback to the rehabilitation specialist or fitness instructor engaging with the user.

As a true sensorimotor experience, the exercise device 10 preferably creates an audible, rhythmic sound when engaged in movement. In one embodiment, as the fluid 24 contained within the casing 18 flows from one end of the device 10 to an opposing end when the device 10 is even slightly tilted, a wave-like sound is emitted by the flowing fluid 24 which creates "white" and "pink" noise depending on the type and speed of movement. Studies have shown the benefits of "white" noise for blocking distractions and enhancing focus and "pink" noise for melting away stress while keeping you energized and alert. Thus, both "white" and "pink" noise are beneficial for exercise and rehabilitation activities.

The overall texture and exterior surface of the casing 18 is preferably constructed of any secure and comfortable grip material, such as but not limited to high quality rubber or textured embedded in the surface that allows for a sanitary and comfortable no slip gripping surface at least across the center member 12. Since the exercise device 10 is meant to be "gripped" by various parts of the body, such as behind the knee and not just in the hands, the tactile sensation associated with touching the exercise device 10 to the skin is of heightened importance and is designed to comfortable and enjoyable to the user.

Quantified measurement of physical activity realized through sensors joined to wireless networks and rendered in a quantitative way to the user through a software application is desirable. As such, in one embodiment, the exercise device 10 preferably includes a sensor (not shown) that can measure and record use metrics, such as but not limited to device levelness, stability, force of fluid flow, and time in use in order to provide feedback into an online or mobile application for training, monitoring and analytical purposes.

EXAMPLE 1

Figure 11:
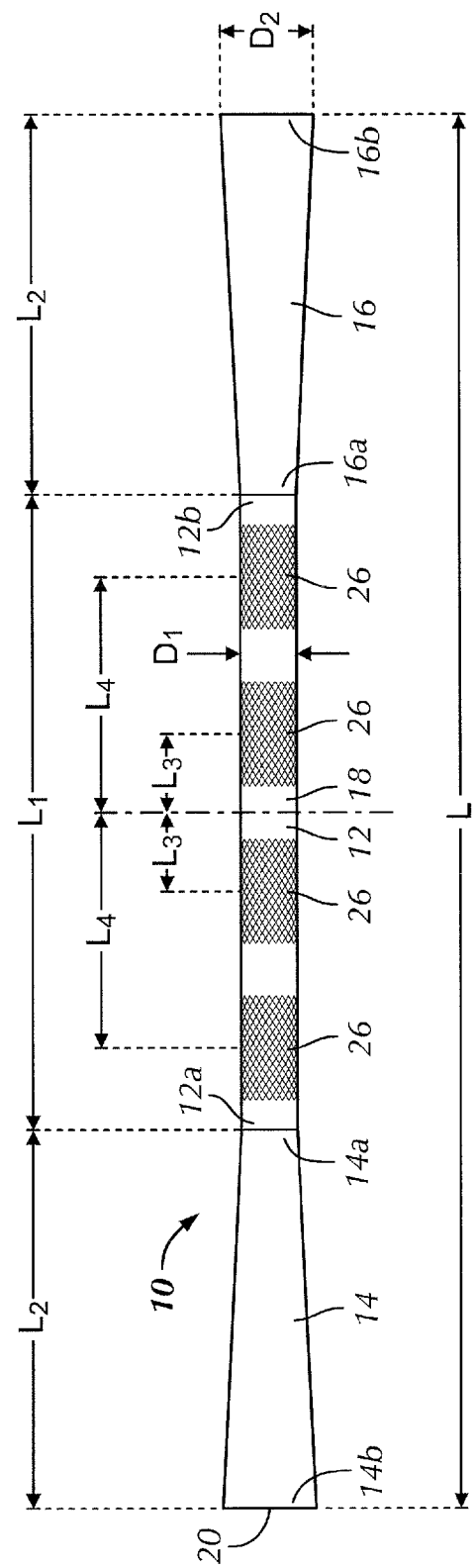
FIG. 11 is a front elevational view of the exercise device in accordance with another preferred embodiment of the present invention.

Referring to FIG. 11, in one embodiment, the exercise device 10 has an overall length L of approximately 48 inches, with a length L1 of the center member 12 being approximately 22 inches and a length L2 of each of the first and second end members 14, 16 being approximately 13 inches. Each of the indicators 26 is in the form of raised projections to give portions of the exterior surface of the casing 18 an embedded texture. A first pair of indicators 26 are equidistant from either side of the midpoint by a first distance L3 and a second pair of indicators 26 are equidistant from either side of the midpoint by a second distance L4 which is larger than L3. The center member 12 and the first ends 14a, 16a of the first and second end members 14, 16 have a diameter D1 of approximately 1.93 inches, while a diameter D2 of the second ends 14b, 16b of the first and second end members 14, 16 is approximately 3.25 inches. The casing 18 has a wall thickness of approximately 0.039 inches. The hollow interior portion of the center member 12 is at least partially filled with approximately 38 ounces of a brine solution. It will be understood that the various dimensions of the exercise device 10 may be altered as necessary to meet the needs and specifications of a particular end use or end user.

A user may engage with the exercise device 10 to receive various benefits. In one embodiment, the user may perform an exercise using the exercise device 10 in order to improve proprioception after suffering from an injury or disability that affects coordination and balance. Therefore, the exercise device 10 can be used to improve motor skills and balance as a faint of therapy. In other cases, an athlete may wish to improve balance for any one of a number of sports requiring a refined sense of balance. Alternatively, the user may use the exercise device 10 more like a standard exercise bar simply to exercise his or her muscles. Also, a user may perform balance training and roller exercises (typical in Pilates classes) using the exercise device 10. There is also the option to just tilt the exercise device 10 back and forth for the simple enjoyment of the swishing sound and movement.

The instability of the exercise device 10 can be increased by moving the grip closer to the center position (i.e., midpoint) of the central member 12. Such a reduced grip spacing leads to increased instability of the exercise device 10 which, in turn, leads to more oscillating motion of the fluid 24 and hence an increased effort to try and restore balance. Conversely, more stability of the exercise device 10 is realized by widening the grip to accommodate an especially difficult routine, or to accommodate a user that is tired, less experienced, or has a low level of stability, such as in a rehabilitation situation. The configuration of the exercise device 10 also allows the exercise device 10 to be adjustable, as the user can continuously and finely adjust the level of difficulty to suit his or her personal needs. As the user's balance, coordination, and endurance improve, the level of difficulty can be increased with various methods, such as changing the angle or distance from the user, changing the user's base of support, or the having the user close his/her eyes.

In one embodiment, the exercise device 10 is used in conjunction with other existing exercise devices, such as a balance ball. This presents a very high level of difficulty and thus requires a high level of agility and balance by the user, which may be appropriate for various forms of athletic training, such as rowing, equestrian training or cross fit.

In one embodiment, the exercise device 10 may be positioned to become relatively stable by taking an extra wide gripping position, resting the exercise device 10 across (or perpendicular to) the longitudinal plane of the user's body (e.g., rested on the user's shoulders), or by positioning the exercise device 10 fully upright in a vertical plane (perpendicular to the horizontal plane P) and resting on the cap 20 of one of the fluted end members 14, 16. In such positions, the user can readily perform ordinary exercises, such as a squat, utilizing the exercise device 10.

The exercise device 10 of the present invention thus preferably provides the user with a method to challenge his/her center of gravity via shifting weight and oscillation of fluid during movement. This creates a whole body reaction which awakens the neural pathways leading to higher brain centers that have a strong influence on controlling equilibrium and posture, maintaining balance and proper function, and decreasing injury risk. The body's response is automatic and involuntary, a reflexive activation of postural stabilizers. The end result is dynamic stability and functional joint stability (i.e., the activation of local stabilizers, the foundation, yet least trained aspect of movement).

The exercise device 10 of the present invention also preferably allows for the integration of typical core stability concepts with the balance and postural control necessary to steady an uneven load and return to the symmetry of a secure central longitudinal axis. Unlike conventional exercise devices, such as gym balls, form rollers, Bosu and other labile training tools, the movements trained by the exercise device 10 are preferably more natural and functional representations of activities of daily living. The versatility of the exercise device 10 lends itself to be used, among other activities, as a full body proprioceptive tool in the open chain, a weight bearing labile tool in the closed chain, a balance aid for standing postures when stood on its end, and the like.

It will also be appreciated by those skilled in the art that changes could be made to the embodiment described above without departing from the broad inventive concepts thereof. Also, based on this disclosure, a person of ordinary skill in the art would further recognize that the relative proportions of the components illustrated could be varied without departing from the spirit and scope of the invention. For example, the size and dimensions of the exercise device 10 and/or the viscosity of the fluid 24 contained within the casing 18 may vary to better accommodate the size, gender, strength, stage of rehabilitation or fitness level of a user. It is understood, therefore, that this invention is not limited to the particular embodiments disclosed, but it is intended to cover modifications within the spirit and scope of the present invention as defined by the appended claims.

We claim:

1. A sensorimotor exercise device comprising:
a casing including an elongated center member having an open first end and an open second end, a first end member provided at the open first end of the center member and a second end member provided at the open second end of the center member; and
a fluid only partially filling a hollow interior of the center member and the first and second end members, the fluid exhibiting a reciprocating movement between the first and second end members through the open first and second ends of the center member, the fluid being irremovably contained within the hollow interior of the center member and the first and second end members, wherein the center member has a cylindrical shape and the first and second end members have a tapered configuration, an inner diameter and an outer diameter of each of the first and second end members increasing from a first end thereof toward an opposing second end thereof.

2. The sensorimotor exercise device according to claim 1, wherein the sensorimotor exercise device is rigid.

3. The sensorimotor exercise device according to claim 1, wherein the first and second end members are of equal length and are mirror images of each other.

4. The sensorimotor exercise device according to claim 1, wherein the sensorimotor exercise device is made from one or more materials selected from the group consisting of fiberglass, composite, plastic, resin and metal.

5. The sensorimotor exercise device according to claim 4, wherein the center member is made from a polymeric material and the first and second end members are made from a linear low density polyethylene.

6. The sensorimotor exercise device according to claim 1, wherein the casing accounts for approximately 20% of the total weight of the sensorimotor exercise device.

7. The sensorimotor exercise device according to claim 1, wherein a diameter of the second end of each of the first and second end members is two to three times larger than a diameter of the center member.

8. The sensorimotor exercise device according to claim 1, wherein the casing is an integral and unitary body.

9. The sensorimotor exercise device according to claim 1, wherein the center member includes tactile, visual and/or audible indicators.

10. The sensorimotor exercise device according to claim 9, wherein the indicators are provided on first and second portions of the center member which are equidistant from either side of a midpoint of the center member.

11. The sensorimotor exercise device according to claim 9, wherein the indicators indicate whether the sensorimotor exercise device is level with respect to a horizontal plane.

12. The sensorimotor exercise device according to claim 11, wherein the indicators are selected from the group consisting of a liquid bubble indicator, laser indicators, light indicators, and vibration of the sensorimotor exercise device.

13. The sensorimotor exercise device according to claim 1, wherein the sensorimotor exercise device creates an audible sound when engaged in movement.

14. The sensorimotor exercise device according to claim 1, wherein a portion of an exterior surface of the casing is formed as a non-slip surface.

15. The sensorimotor exercise device according to claim 1, wherein a portion of an exterior surface of the casing includes an embedded texture to form a non-slip surface.

16. The sensorimotor exercise device according to claim 1, wherein the fluid has a viscosity of 0.5 to 100 cP.

17. The sensorimotor exercise device according to claim 16, wherein the fluid has a viscosity of 0.5 to 7 cP.

18. The sensorimotor exercise device according to claim 1, wherein the fluid has a density of 0.8 to 3 g/mL.

19. The sensorimotor exercise device according to claim 1, wherein the inner diameter of the first end of each of the first and second end members is the same as an inner diameter of the center member.

20. The sensorimotor exercise device according to claim 1, wherein the first end of each of the first and second end members is an open end, such that the interiors of the first and second end members are in communication with the hollow interior of the center member.

21. The sensorimotor device according to claim 1, wherein the outer diameter of the first end of each of the first and second end members is the same as an outer diameter of the center member.

22. The sensorimotor device according to claim 1, wherein the casing is translucent.

* * * * *